US00PP20216P2

(12) United States Plant Patent
Geerlings

(10) Patent No.: US PP20,216 P2
(45) Date of Patent: Aug. 11, 2009

(54) ***PHLOX* PLANT NAMED 'VALENTINA'**

(50) Latin Name: *Phlox paniculata*
Varietal Denomination: Valentina

(75) Inventor: Peter Geerlings, Hillegom (NL)

(73) Assignee: Compass Plants B.V., Hillegom (NL)

( * ) Notice: Subject to any disclaimer, the term of this patent is extended or adjusted under 35 U.S.C. 154(b) by 0 days.

(21) Appl. No.: 12/214,229

(22) Filed: Jun. 16, 2008

(51) Int. Cl.
*A01H 5/00* (2006.01)

(52) U.S. Cl. ..... Plt./320

(58) Field of Classification Search ..... Plt./320
See application file for complete search history.

*Primary Examiner*—Annette H Para
(74) *Attorney, Agent, or Firm*—C. A. Whealy

(57) ABSTRACT

A new and distinct cultivar of *Phlox* plant named 'Valentina', characterized by its upright plant habit; freely flowering habit; soft pink-colored flowers; and good cut flower and garden performance.

2 Drawing Sheets

Botanical designation: *Phlox paniculata.*
Cultivar denomination: 'VALENTINA'.

BACKGROUND OF THE INVENTION

The present invention relates to a new and distinct cultivar of *Phlox*, botanically known as *Phlox paniculata* and hereinafter referred to by the name 'Valentina'.

The new *Phlox* originated from a cross-pollination of two unnamed proprietary selections of *Phlox paniculata,* not patented. The new *Phlox* was discovered and selected by the Inventor as a single flowering plant from within the progeny of the stated cross-pollination grown in a controlled greenhouse environment in Hillegom, The Netherlands in July, 2004.

Asexual reproduction of the new *Phlox* by cuttings in a controlled greenhouse environment in Hillegom, The Netherlands since 2006, has shown that the unique features of this new *Phlox* are stable and reproduced true to type in successive generations.

SUMMARY OF THE INVENTION

Plants of the new *Phlox* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Valentina'. These characteristics in combination distinguish 'Valentina' as a new and distinct cultivar of *Phlox*:

1. Upright plant habit.
2. Freely flowering habit.
3. Soft pink-colored flowers.
4. Good cut flower and garden performance.

Plants of the new *Phlox* and the parent selections differ primarily in plant height and flower color.

Plants of the new *Phlox* can also be compared to plants of *Phlox paniculata* 'Starfire', not patented. In side-by-side comparisons conducted in Hillegom, The Netherlands, plants of the new *Phlox* and 'Starfire' differed primarily in flower color as plants of 'Starfire' had bright red-colored flowers. In addition, plants of the new *Phlox* were shorter than plants of 'Starfire'.

BRIEF DESCRIPTION OF THE PHOTOGRAPHS

The accompanying colored photographs illustrate the overall appearance of the new *Phlox*, showing the colors as true as it is reasonably possible to obtain in colored reproductions of this type. Colors in the photographs may differ slightly from the color values cited in the detailed botanical description which accurately describe the colors of the new *Phlox*.

The photograph on the first sheet comprises a side perspective view of a typical flowering plant of 'Valentina' grown in a container.

The photograph at the top of the second sheet is a close-up view of typical flowers of 'Valentina'.

The photograph at the bottom of the second sheet is a close-up view of a typical leaves of 'Valentina'.

DETAILED BOTANICAL DESCRIPTION

The aforementioned photographs and following observations, measurements and values describe plants grown in Hillegom, The Netherlands, under commercial practice during the late summer and early autumn in an outdoor nursery with day temperatures ranging from 14° C. to 32° C. and night temperatures ranging from 5° C. to 15° C. Plants had been growing for two years when the photographs and description were taken. In the following description, color references are made to The Royal Horticultural Society Colour Chart, 2001 Edition, except where general terms of ordinary dictionary significance are used.

Botanical classification: *Phlox paniculata* 'Valentina'.
Parentage:

*Female, or seed, parent.*—Unnamed proprietary selection of *Phlox paniculata,* not patented.

*Male, or pollen, parent.*—Unnamed proprietary selection of *Phlox paniculata,* not patented.

Propagation:

*Type.*—By cuttings.

*Time to initiate roots.*—About three weeks at 20° C.

*Root description.*—Fine, fibrous; white in color.

Plant description:

*Plant form/habit.*—Upright plant habit; narrow inverted triangle;

moderately vigorous growth habit. Basally branching habit, about ten basal branches per plant.

*Plant height.*—About 43.2 cm.

*Plant width* (*spread*).—About 45 cm.

*Lateral branches.*—Length: About 19.6 cm. Diameter: About 5 mm. Internode length: About 2.3 cm. Strength: Strong. Texture: Smooth, glabrous. Color: Close to N186C.

Foliage description:

*Arrangement.*—Opposite, simple.

*Length.*—About 9.6 cm.

*Width.*—About 3 cm.

*Shape.*—Elliptic to narrowly ovate.

*Apex.*—Apiculate.

*Base.*—Obtuse.

*Margin.*—Slightly revolute and finely serrate.

*Texture, upper and lower surfaces.*—Smooth, glabrous.

*Venation pattern.*—Pinnate.

*Color.*—Developing leaves, upper surface: Close to N186A. Developing leaves, lower surface: Close to N187A, towards the base, close to 146B. Fully expanded leaves, upper surface: Between 137A and 146A slightly tinged with close to N186A; venation, close to N187A. Fully expanded leaves, lower surface: Close to 146C flushed with close to N187B to N187C; venation, close to 187A to 187B.

*Petiole.*—Length: About 3 mm. Diameter: About 3 mm by 2 mm. Texture, upper and lower surfaces: Smooth, glabrous. Color, upper surface: Close to 187A to 187B. Color, lower surface: Close to N187A.

Flower description:

*Flower type/habit.*—Single rotate and salverform flowers arranged in compound terminal panicles; flowers face upright and outward. Panicles roughly conical in shape. Freely flowering habit with about 180 flower buds and flowers developing per inflorescence.

*Fragrance.*—Moderately fragrant; sweet and pleasant.

*Natural flowering season.*—Continuously flowering from July until late August in The Netherlands. Flowers not persistent.

*Postproduction longevity.*—Flowers last about ten days on the plant.

*Flower buds.*—Height: About 2.1 cm. Diameter: About 5 mm. Shape: Oblanceolate. Color: Close to 62A to 62B.

*Inflorescence height.*—About 19.4 cm.

*Inflorescence diameter.*—About 18.9 cm.

*Flower diameter.*—About 2.9 cm.

*Flower depth.*—About 2.5 cm.

*Petals.*—Quantity per flower: Typically five in a single whorl; petals fused at the base into a narrow tube. Length: About 3.4 cm. Lobe width: About 1.5 cm. Shape: Spatulate. Apex: Obtuse. Margin: Entire. Texture, upper and lower surfaces: Smooth, glabrous. Color: Developing petals, upper surface: Close to 68C; towards the base, close to N74A to N74B; throat, close to 76A to 76B. Developing petals, lower surface: Close to 73D; tube, close to 76A. Fully expanded petals, upper surface: Between 73B to 73C and 75B; towards the base, close to N78B; throat, close to 76A. Fully expanded petals, lower surface: Close to 75C to 75D; tube, close to 76A.

*Sepals.*—Quantity per flower: Typically five in a single whorl, fused towards the base; campanulate calyx. Length: About 1.1 cm. Width: About 3 mm. Shape: Lanceolate. Apex: Narrowly apiculate. Margin: Entire. Texture, upper and lower surfaces: Smooth, glabrous. Color, developing sepals, upper and lower surfaces: Close to 187A. Color, fully expanded sepals, upper and lower surfaces: Close to 187A; towards the base, close to 146C to 146D.

*Peduncles.*—Length: About 16.5 cm. Diameter: About 3 mm. Angle: Erect to about 50° from vertical. Strength: Strong. Texture: Smooth, glabrous. Color: Close to N186C.

*Pedicels.*—Length: About 4 mm. Diameter: About 1 mm. Angle: About 30° from vertical. Strength: Strong. Texture: Smooth, glabrous. Color: Close to N186C flushed with close to 147B to 147C.

*Reproductive organs.*—Stamens: Quantity per flower: Typically five; fused with petals in throat. Filament length: About 1 mm. Anther shape: Oblong. Anther length: About 1.5 mm. Anther color: Close to 4D. Pollen amount: Scarce to moderate. Pollen color: Close to 4C. Pistils: Quantity per flower: One. Pistil length: About 1.9 cm. Stigma shape: Three-parted. Stigma color: Close to 150C to 150D. Style length: About 1.8 cm. Style color: Close to 147C to 147D. Ovary color: Close to 143A.

*Seed/fruit.*—Seed and fruit development have not been observed.

Disease/pest resistance:

Plants of the *Phlox* have not been observed to be resistant to pathogens and pests common to *Phlox*.

Garden performance:

Plants of the new *Phlox* have been observed to have good garden performance and tolerate rain, wind and temperatures ranging from about −30° C. to about 30° C.

It is claimed:

1. A new and distinct *Phlox* plant named 'Valentina' as illustraded and described.

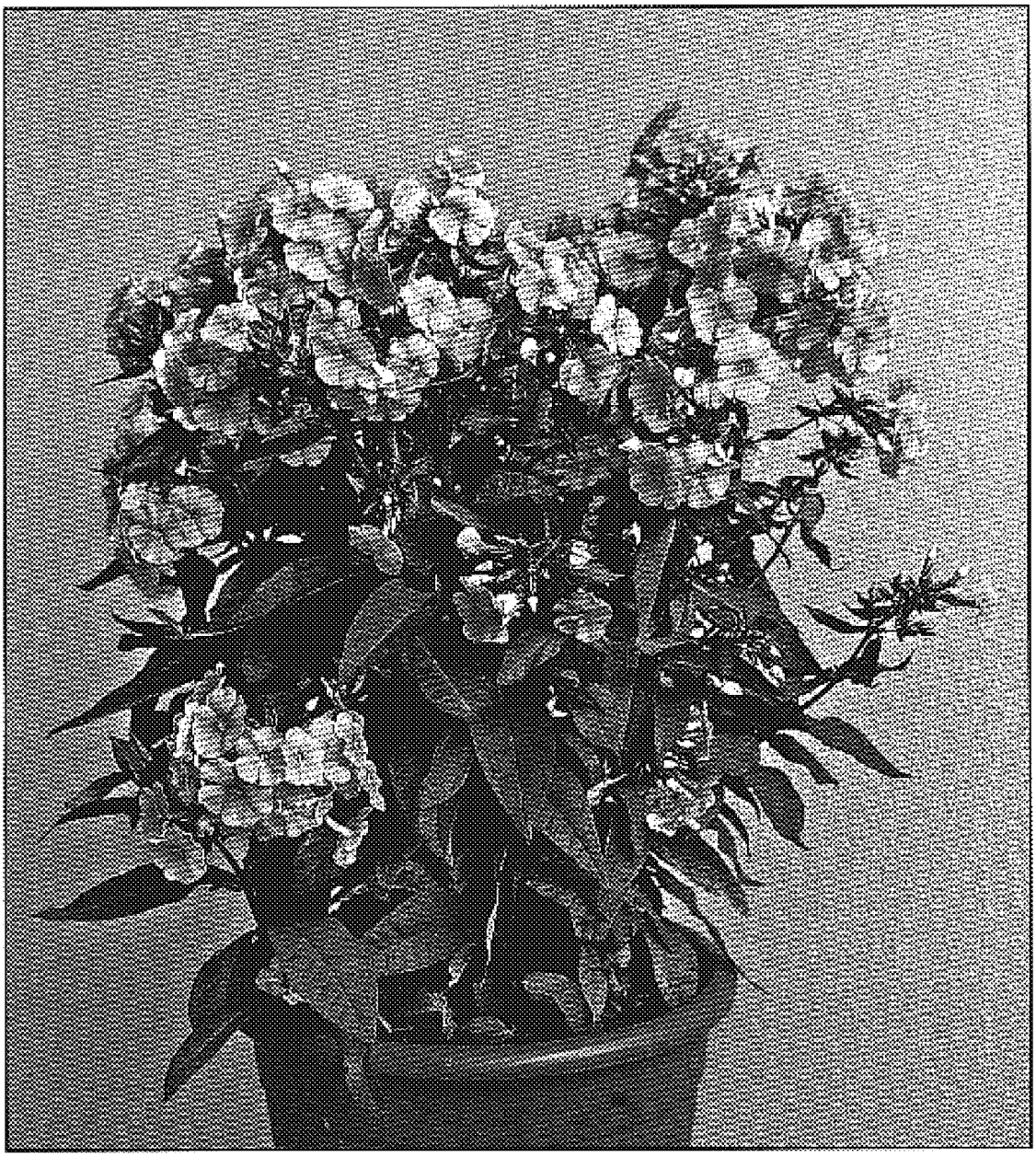

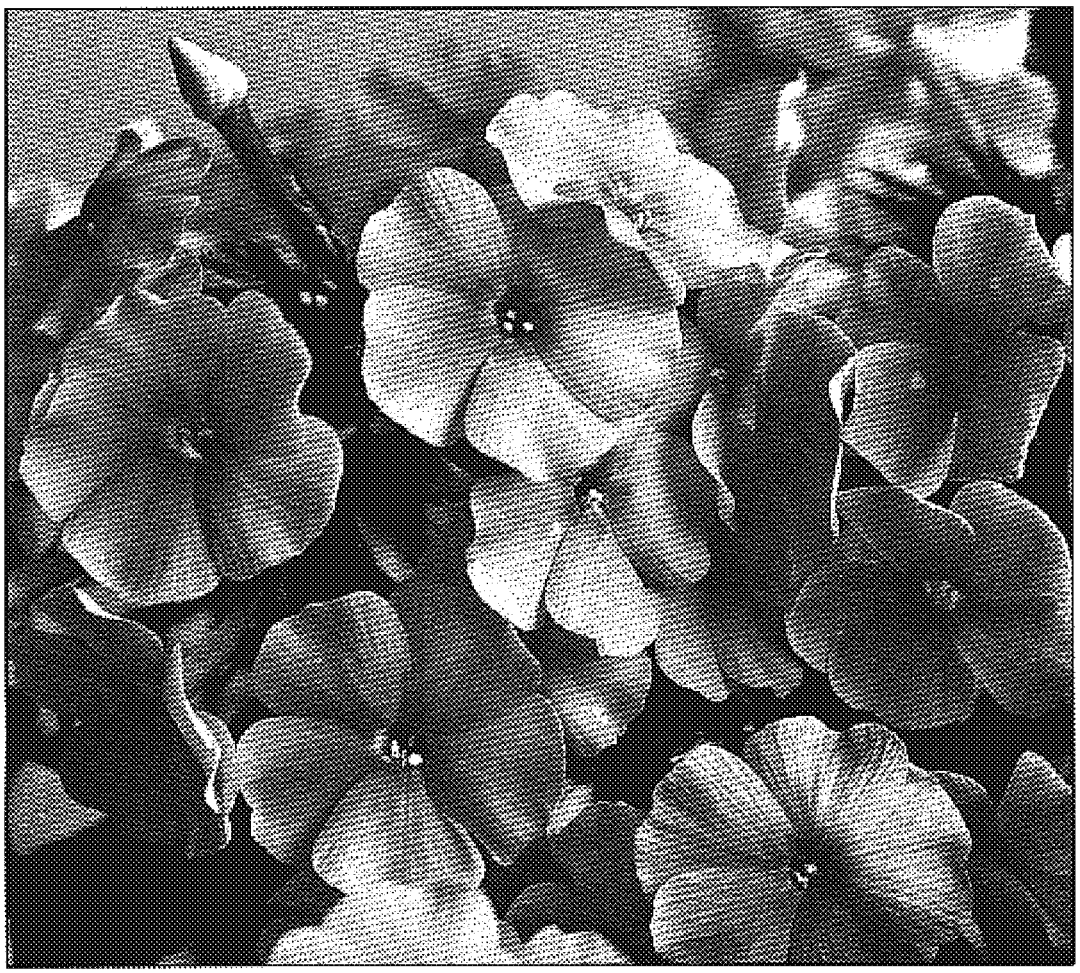
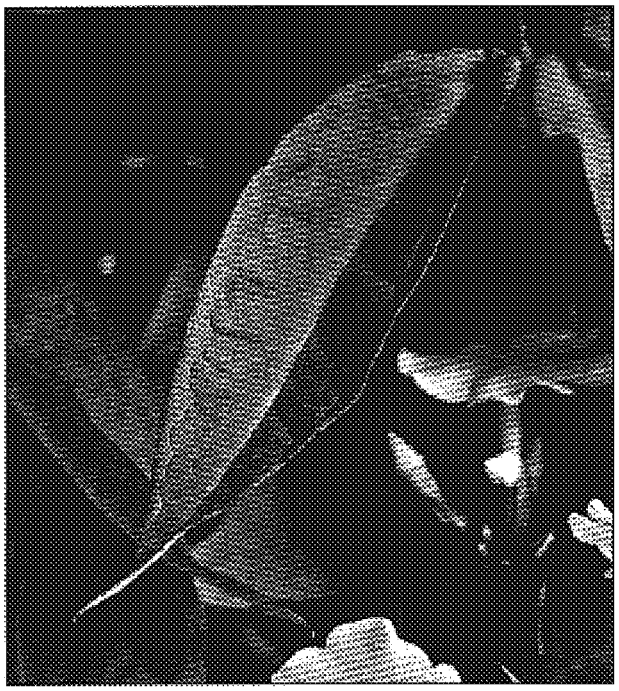

* * * * *